US009910006B2

(12) United States Patent
Zilly et al.

(10) Patent No.: US 9,910,006 B2
(45) Date of Patent: Mar. 6, 2018

(54) METHOD FOR MANUFACTURING A GLASS ASSEMBLY AND APPARATUS FOR EXECUTING THE METHOD

(71) Applicant: Endress + Hauser Conducta Gesellschaft für Mess- und Regeltechnik mbH + Co. KG, Gerlingen (DE)

(72) Inventors: Roland Zilly, Jahnsdorf (DE); Carsten Enderwitz, Waldheim (DE); Torsten Zeidler, Radebeul (DE); Ronny Kuhn, Waldheim (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 36 days.

(21) Appl. No.: 14/935,805

(22) Filed: Nov. 9, 2015

(65) Prior Publication Data

US 2016/0137541 A1 May 19, 2016

(30) Foreign Application Priority Data

Nov. 13, 2014 (DE) .................. 10 2014 116 579

(51) Int. Cl.
*C03B 9/40* (2006.01)
*G01N 27/28* (2006.01)
(Continued)

(52) U.S. Cl.
CPC .......... *G01N 27/283* (2013.01); *C03B 7/005* (2013.01); *C03B 7/22* (2013.01); *C03B 9/41* (2013.01);
(Continued)

(58) Field of Classification Search
CPC .. C03B 9/403; C03B 9/41; C03B 9/32; C03B 7/22; C03B 7/005
See application file for complete search history.

(56) References Cited

U.S. PATENT DOCUMENTS 2,346,470 A * 4/1944 Cary .................. C03B 9/02
204/420
3,490,889 A * 1/1970 Goto .................. C03B 23/20
264/272.12
(Continued)

FOREIGN PATENT DOCUMENTS

DE 10116075 C1 5/2002
DE 10116099 A1 10/2002
JP 61036141 A * 2/1986

OTHER PUBLICATIONS

DE 10116099 machine translation, Production of an expanded glass body used as a component of an electrochemical sensor, Oct. 2, 2002.*

(Continued)

Primary Examiner — Queenie S Dehghan
(74) Attorney, Agent, or Firm — Christopher R. Powers; PatServe

(57) ABSTRACT

A method for manufacturing a glass assembly comprises the steps: lowering of a dip pipe that gas may flow through vertically to the surface of a glass melt; determining when the surface of the glass melt is encountered by the dip pipe end showing towards the glass melt by detecting an increase of the gas pressure found inside the dip pipe; continued lowering of the dip pipe until a predetermined depth of entry of the dip pipe end showing towards the glass melt is reached; obtaining a predetermined pressure inside the dip pipe while the dip pipe first stays at the given immersion depth for the given duration and after the predetermined duration is completed, is lifted with a given speed vertically to the surface of the glass melt, thus creating a gas bubble in the glass melt whose walls are attached to the end of the dip pipe; continued lifting of the dip pipe vertically to the surface of the glass melt until the gas bubble is separated from the glass melt, with the wall of the gas bubble (Continued)

remaining at the dip pipe end as a closing film; and setting, especially controlling and/or adjusting of the pressure inside the dip pipe based on the geometry of the film closing the end of the dip pipe as determined by an image capturing device.

13 Claims, 3 Drawing Sheets

(51) Int. Cl.
      *C03B 9/41*     (2006.01)
      *C03B 7/22*     (2006.01)
      *C03B 7/00*     (2006.01)
      *G01N 27/30*     (2006.01)
      *G01N 27/333*     (2006.01)

(52) U.S. Cl.
    CPC ......... *G01N 27/302* (2013.01); *G01N 27/333* (2013.01)

(56) References Cited

U.S. PATENT DOCUMENTS 6,848,271 B2     2/2005   Auras
8,562,801 B2 *  10/2013  Boeck ................ G01N 21/8507
                                                                              204/433

OTHER PUBLICATIONS

German Search Report, German Patent Office, Munich, DE, dated May 18, 2015.

\* cited by examiner

METHOD FOR MANUFACTURING A GLASS ASSEMBLY AND APPARATUS FOR EXECUTING THE METHOD

TECHNICAL FIELD

The invention concerns a method for manufacturing a glass assembly, especially a glass wall or assembly of an electrochemical sensor, for example a pH sensor or another ion-selective sensor.

BACKGROUND DISCUSSION

Electrochemical, especially potentiometric sensors may include an ion-selective membrane in which a potential depending on the concentration of a certain type of ions develops during operation. The most popular example of such a sensor is the potentiometric combination electrode with a pH glass electrode. This includes a membrane made of a pH-selective glass which usually is lightly blow-attached to the end of a tube-like glass shaft, with the membrane closing the shaft at one end. Inside the shaft, there is an internal liquid or thickened, gel-type electrolyte that touches the membrane and usually includes a buffer system to set the electrolyte to a predetermined pH value. For measuring, the glass membrane is put in contact with a measuring liquid, which causes a hydrated layer to develop at the border to the measuring liquid that may accept or release hydronium ions ($H^+$ or $H_3O^+$). At the borderline between the membrane glass and the measuring liquid, a dissociation occurs during which the alkali ions of the membrane glass are replaced by $H^+$ ions from the measuring liquid, thus creating a plurality of hydroxyl groups in the hydrated layer. Depending on the pH value of the measuring liquid, $H^+$ ions either diffuse from the hydrated layer, or into the hydrated layer. During measuring operation of the glass electrode, this occurs both on the surface of the membrane touching the measuring liquid and on the opposite surface of the membrane touching the internal electrolyte. Since the internal electrolyte shows a constant pH value, there is a potential difference via the membrane that is dependent on the pH value of the measuring medium. Details on the design and function of a glass electrode for pH measuring are known from H. Galster, "pH-Messung, Grundlagen, Methoden, Anwendungen, Geräte", VCH Verlagsgesellschaft, Weinheim, 1990. The book also names suitable membrane glasses.

Depending on the type of measuring task the sensor may be used for, a wide range of membrane geometries are used. The spherical or spherical cap form is very common. However, cone-shaped membranes or flat membranes are desired for certain measuring tasks.

The manufacture of electrochemical sensors by their nature usually includes the generation of an ion-selective membrane and an assembly that includes a shaft connected to the membrane. For the glass electrodes as described above, a glass assembly is constructed by connecting the membrane made of analyte-sensitive glass, especially of a pH-sensitive glass to a glass shaft by slightly melting or blowing it. This glass assembly is then connected to other components of the sensor.

Such a glass assembly with an analyte-sensitive membrane, especially including a spherical or spherical cap form, may be manufactured manually using craftsman's glass blowing techniques, by placing a tubular, usually cylindrical body, in the following referred to as the dip pipe, into molten glass. When it is subsequently pulled out, it takes a roughly determined amount of liquid glass with it from the glass melt. The glass blower then feeds air into the dip pipe with his/her mouth, which allows the sphere or spherical cap to be blown from the absorbed amount of molten viscous glass. This process requires skill and experience as a glass blower.

From German Patent, DE 101 16 099 B4, a method and automated apparatus to manufacture a glass assembly is known. This procedure allows a dip pipe to be lowered in the direction of the surface of a glass melt, and the point of reaching the surface is determined by detecting an increase of the gas pressure inside the dip pipe when the dip pipe touches the surface of the glass melt. The dip pipe is then controlled to have its free end lowered to a certain, predetermined table dip depth in the glass melt, and then is pulled out again, taking a predetermined amount of molten glass with it in the process. A pump is then used to control the gas pressure inside the dip pipe after the dip pipe is pulled out of the glass melt according to a gas pressure curve saved in the controls that generates a spherical or spherical cap glass membrane from the molten membrane glass absorbed by the dip pipe.

The method known from DE 101 16 099 B4 which can automatically be executed by the apparatus described there, is, however, not suitable for the manufacture of flat membranes.

SUMMARY OF THE INVENTION

This invention therefore intends to describe a method that allows the automated manufacture of a glass assembly with a flat membrane.

This task is solved by a method to create a glass assembly which comprises the steps:
  lowering of a dip pipe, especially one that gas can flow through, vertically to the surface of a glass melt;
  determining when the surface of the glass melt is encountered by the dip pipe end showing towards the glass melt by detecting an increase of the gas pressure found inside the dip pipe;
  continued lowering of the dip pipe until a predetermined depth of entry of the dip pipe end showing towards the glass melt is reached;
  obtaining a predetermined pressure inside the dip pipe while the dip pipe first stays at the given immersion depth for the given duration and after the predetermined duration is completed, is lifted with a given speed vertically to the surface of the glass melt, thus creating a gas bubble in the glass melt whose walls are attached to the end of the dip pipe;
  continued lifting of the dip pipe vertically to the surface of the glass melt until the gas bubble is separated from the glass melt, with the wall of the gas bubble remaining at the dip pipe end as a closing film;
  setting, especially controlling and/or adjusting of the pressure inside the dip pipe based on the geometry of the film closing the end of the dip pipe as determined by an image capturing device.

This method allows for the creation of a membrane closing the dip pipe that has a low degree of curvature, especially a flat membrane. In the method known from DE 101 16 099 B4, a certain amount of glass melt is absorbed that then remains on the dip pipe when the dip pipe is pulled out of the glass melt like a blanking plug. Only when pressure is applied to the inside of the dip pipe, this plug turns into a thin membrane which naturally shows a strong curvature, i.e. a spherical cap or spherical form. In contrast to this, the dip pipe is impinged with a given pressure in the method according to the invention, while its end is still immersed in the glass melt and then is pulled from the glass melt by lifting it. Thus, a gas bubble is generated in the glass melt whose walls are attached to the end of the dip pipe. If the dip pipe is still lifted until the gas bubble becomes detached from the glass melt, a film of glass melt develops that closes the dip pipe. The geometry of said film may be determined by the pressure inside the dip pipe. If the pressure in the dip pipe is adjusted in such a way that the film shows only very little curvature, the film becomes a flat membrane once it is solidified.

In one embodiment of the method, the predetermined pressure applied to the inside of the dip pipe while the dip pipe remains at the given dip depth for a given time and then after the end of the immersion time is lifted with the predetermined speed vertically to the surface of the glass melt, follows a blow pressure curve saved in an electronic control device. The curve shows the pressure as a function of the time.

The predetermined speed used to lift the dip pipe during the application of a predetermined pressure according to the blow pressure curve may follow a given speed curve saved in an electronic control device that states the speed as a function of time or as a curve of movement which states the position of the dip pipe and/or the end of the dip pipe pointing towards the glass melt with regard to the surface of the glass melt as a function of time.

Continued lifting of the dip pipe until the gas bubble separates from the glass melt may be completed with an increased speed.

Any adjustment of the pressure applied to the inside of the dip pipe on the basis of the geometry of the film closing the end of the dip pipe as captured by the image capturing device may be done by recording the actual geometry (current state) of the film by the image capturing device and comparing it to the saved target data that specify a target geometry of the film using a calculation program and an image processing device. The given target data may, for example, be used to describe the geometry of a flat membrane.

The geometry of the flat membrane may, for example, be predetermined in such a way that no point of the flat membrane shows a distance from an imaginary line that is vertical to the axis of the pipe through a connection point of the membrane with the dip pipe which is larger than 30%, preferably larger than 20%, still more preferably larger than 10% of the external diameter of the dip pipe.

The dip pipe used is preferably a glass pipe.

The pressure on the inside of the dip pipe can be controlled and/or adjusted until the film closing the end of the dip pipe has solidified to a firm membrane through cooling after leaving the glass melt, especially a flat membrane.

Once the film closing the end of the dip pipe has solidified into a firm membrane, especially a flat membrane, a comparison between the geometry of the membrane obtained with the image capturing device and the saved target data that specifies a target membrane geometry serves to classify the glass assembly. This classification may, for example, be conducted in such a way that the glass assembly is classified as a reject or that, depending on the degree to which it is close to the target status, is assigned a quality class selected from a group of quality classes.

The glass assembly composed of dip pipe and membrane may be manufactured as a wall, enclosure component or assembly of an electrochemical sensor.

The parameters of immersion depth, duration and/or speed for lifting and pulling the dip pipe out of the glass melt may be saved in a control device controlling the process, especially a computer, a programmable logic controller or another electronic data processing device as selectable data and a device causing the lowering and lifting of the dip pipe can be controlled accordingly.

The invention also includes an automated apparatus to execute the method according to one of the claims above, including:
  a glass melting device with an access opening;
  a dip pipe;
  a setting device to lower, immerse and lift the dip pipe vertically to the surface of a glass melt contained in the glass melting device;
  a pressure measuring device that detects any pressure increase inside the dip pipe when the dip pipe touches the surface of the glass melt;
  a pressure setting device to apply a pressure to the inside of the dip pipe; and
  a control device to control the setting device and to control the pressure setting device, with the control device including an operating program that serves to execute the method according to one of the embodiments mentioned above, and the control device being equipped to execute the operating program.

The pressure setting device may, for example, include a pump device. The glass melting device may be a heatable crucible.

The device may further include an image capturing device and an image processing device to capture the geometry of the film closing the end of the dip pipe. The image capturing device may for example include a digital camera that is positioned in such a way that it can capture the end of the dip pipe closed by the film when it is pulled out of the melt. The image processing device may include an electronic data processing device, and may especially be part of the control device mentioned before. The image processing device further includes a computational program that generates data suitable for a target/actual comparison from the image data captured by the image capturing device and/or executes the comparison. In addition, it proves to be advantageous if the image capturing device has a display device and is equipped to display the image data captured via the actual geometry of the membrane on the display device, especially a monitor, preferably against the backdrop of the target data to be achieved.

BRIEF DESCRIPTION OF THE DRAWINGS

The invention is explained in further detail below on the basis of the embodiments shown in the illustrations. They show.

DETAILED DISCUSSION IN CONJUNCTION WITH THE DRAWINGS

Figure 1:
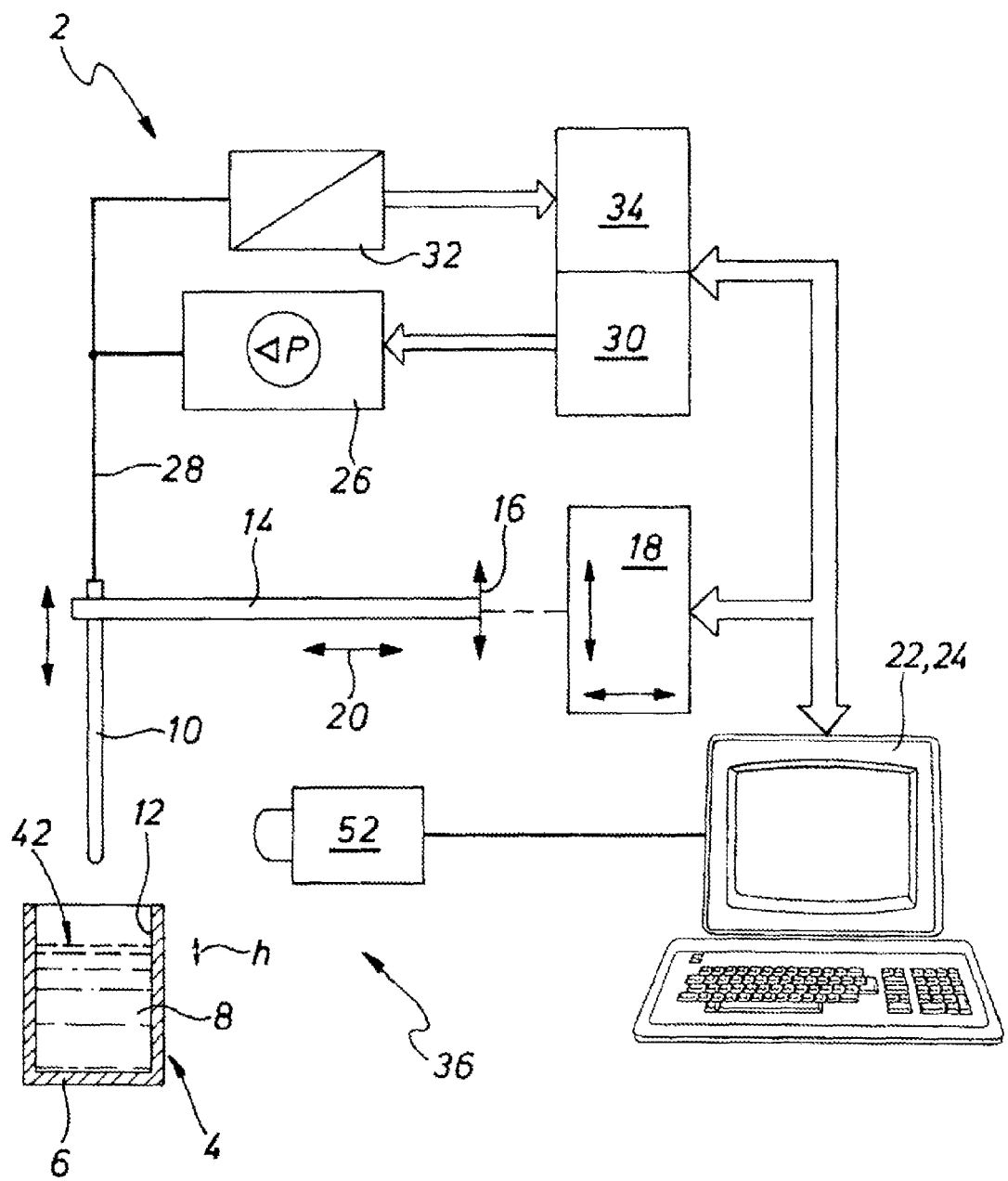
FIG. 1 is a schematic representation of an apparatus for the automated manufacture of a glass assembly that features a glass pipe and a flat membrane closing the glass pipe at one end.

FIG. 1 shows an apparatus 2 to create a glass assembly. The apparatus 2 comprises a glass melting device 4, which consists, for example of a crucible 6, especially heated by an induction coil that is not shown, that receives the glass melt 8. Furthermore, the apparatus comprises a dip pipe 10, which may be a glass pipe. The glass pipe may, but does not necessarily have to have a cylindrical symmetry. The dip pipe 10 can be inserted into the crucible 6 via an opening 12, and be immersed into the glass melt 8. Immersing the dip pipe 10 into the glass melt 8 is achieved by lowering a holding device 14 for the dip pipe in the direction of the double arrow 16, i.e. towards the level of the glass melt 48. For this purpose, the apparatus 2 comprises a setting device 18, which may, if necessary, also be able to follow a movement along the direction of the double arrow 20, i.e. vertically to the lowering direction.

The setting device 18 is connected to a control device 22 which in the present example is implemented as a computer, including an operation program it may execute that is used to control the movement of the setting device 18. For this purpose, the setting device 22 includes a memory in which the operating program may be saved, as well as a processor that can access the memory to execute the operating program.

The apparatus 2 further comprises a pressure setting device 26 to apply an adjustable gas pressure on the inside of the dip pipe 10. The pressure setting device 26 may, for example, include a pump device. The connection between the pump device 26 and the end of the dip pipe 10 that is pointing away from the glass melt 8 is achieved via a flexible hose 28. The pressure setting device 26 is controlled by the control device 22 via a data transfer device 30. Furthermore, provision is made for a pressure measurement device 32 in the form of a pressure sensor that captures the pressure applied on the inside of the dip pipe 10 and transfers it to the control device 22 via a transfer device 34.

The pressure measurement 32 in connection with the computer-supported control device 22 forms a device 36 to determine the position of the glass melt 8 surface in the crucible 6. If, for example, a continuous, comparably very small gas or air flow is passed through the hose 28 and the dip pipe 10 by the pressure setting device 26 that leaves the dip pipe at the latter's free end, at the moment the free end of the dip pipe 10 touches the surface 42 of the glass melt while the holding fixture 14 is lowered in the direction of the melt 8 a pressure increase occurs inside the dip pipe. This pressure increase can be determined using the pressure sensor 32 and be passed on to the control device 22 via the transfer device 34. This allows an exact determination of when the surface of the glass melt 8 is reached. It is now possible to control the setting device 18 in such a way that the dip pipe 10 is lowered into the glass melt 8 up to an exact immersion depth h lower than the level 42.

The same result may, however, also be achieved if no continuous air or gas flow is passed through the hose 28 or the dip pipe 10 respectively. As it approaches the hot, liquid glass melt, the air or gas volume inside the dip pipe 10 increases, resulting in a spontaneous pressure increase inside the dip pipe which may also be detected by the pressure measuring device 32 or the pressure sensor respectively and be used for the control functions as described above.

Including the pressure measuring device 32 into the control of the pump device further allows the generation of a control circuit that can serve to very precisely follow a blow pressure curve p(t) saved in the memory of the control device 22. The determination of the moment of reaching the surface of the glass melt according to one of the methods described above and the execution of the blow pressure curve may be done using the control device 22 with the operating program.

The apparatus 2 further comprises an image capturing device 52, e.g. a digital camera that is connected to the control device 22 so that the image data captured by the image capturing device, or processed image data may be transferred to the control device 22. The control device 22 includes an operating program that serves to process the image data, especially to compare the image data with target data saved in the memory of the control device 22. In the example shown here, the control device 22 therefore simultaneously functions as an image processing device. In an alternative embodiment it is, however, also possible to provide a further data processing device in addition to the control device 22 that serves as an image processing device and is connected with the control device for communication purposes to transfer the results of the comparison of the captured image data with the saved target data to the latter device.

Figure 2:
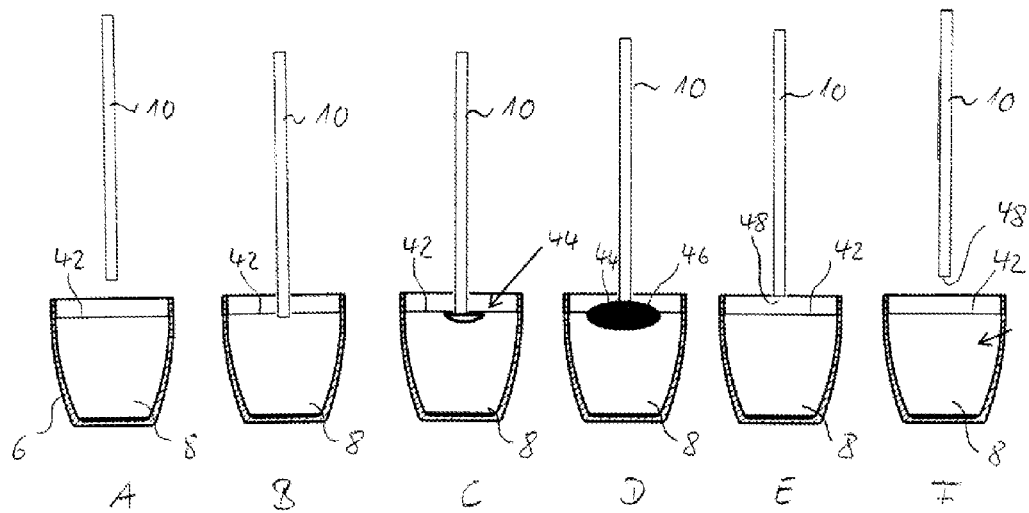
FIG. 2 is a schematic representation of individual process steps during the creation of a glass assembly.
Figure 3:
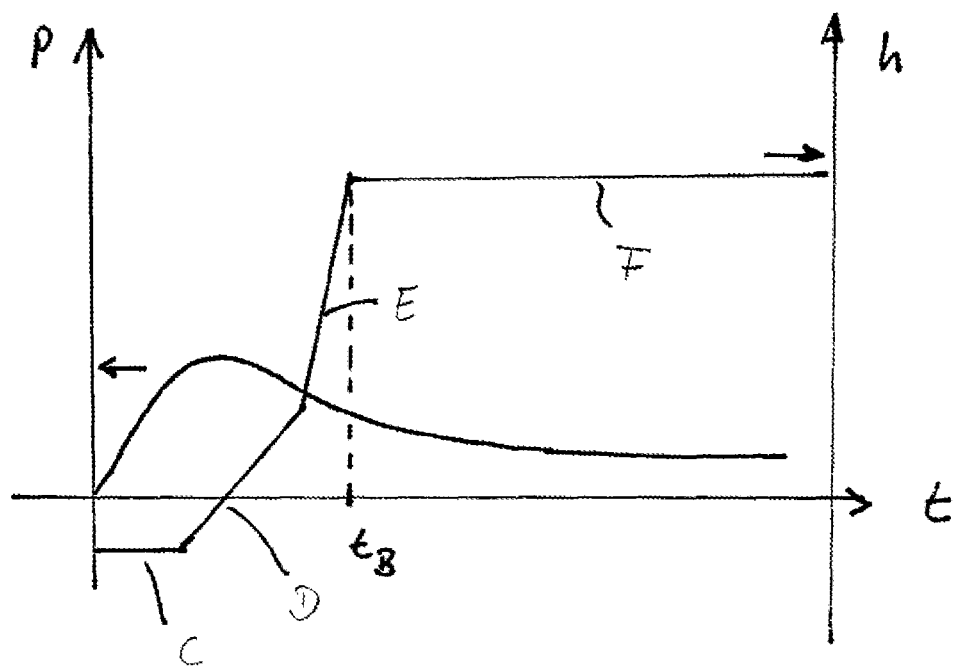
FIG. 3 is a schematic representation of a blow pressure curve p(t) and a movement curve h(t) of the dip pipe that serve to generate a flat membrane closing the dip pipe according to the process shown in FIG. 2.

In the following, a method for the automated production of a glass assembly with a glass pipe and a membrane closing the glass pipe at one end using the apparatus 2 shown in FIG. 1 is described based on FIGS. 2 and 3. The schematic representation in FIG. 2 only shows the glass pipe serving as the dip pipe 10 and the crucible 6 with the glass melt 8. FIG. 3 is a schematic representation of a gas pressure curve p(t) and a movement curve h(t) that shows the height of the free end of the dip pipe 10 pointing towards the glass melt 8 in relation to the level 42 of the glass melt, each one depicted as a function of time. The segments of the movement curve marked with the letters B, C, D and E in FIG. 3 correspond to the process steps B, C, D and E schematically depicted in FIG. 2.

The glass pipe to which a membrane is to be applied is first fixed in the holding device 14 as a dip pipe 10 and connected to the pressure setting device at one end via the hose 28. First, the dip pipe 10 is heated for a set preheating period by holding it at a set, small distance above the hot glass melt 8. The distance may be just a few millimeters. The dip pipe 10 is then lowered in step A vertically to the surface of the glass melt 8 by controlling the setting device accordingly. The pipe axis, which may, for example, be a cylindrical symmetry axis of the dip pipe 10, runs mainly vertically to the surface 42 of the glass melt 8. While the dip pipe 10 is lowered, the pressure inside the dip pipe 10 or the hose 28 respectively is determined by the pressure measuring device 32 and passed on to the control device 22 via the transfer device 34. The moment the melt surface 42 touches the free end of the dip pipe 10, the air outlet is closed and the pressure inside the dip pipe 10 increases. This pressure increase indicates to the control device 22 that the melt surface 42 has been reached.

Once it has determined that the melt surface 42 has been reached, the control device 22 manipulates the setting device 18 in such a way that the dip pipe 10 is immersed into the glass melt 8 at a predetermined immersion depth h (step B). The dip pipe 10 remains in this position for a predetermined duration. During this retention period, the control device 22 controls the pressure setting device 26 via the transfer device 30 to gradually increase the pressure p inside the dip pipe 10 according to a blow pressure curve p(t) saved in the control device, see FIG. 3. Due to the high viscosity of the glass melt 8, a gas bubble 44 develops whose wall is attached to the front end of the dip pipe 10 (step C).

Once the retention period is over, the control device 22 controls the setting device 18 to lift the dip pipe 10 with a set first speed corresponding to the gradient of the curve section of the movement curve h(t) marked with the letter D vertically to the surface of the glass melt while it continues to control the pressure inside the dip pipe 10 according to the blow pressure curve p(t) (FIG. 3).

During this process, the gas bubble 44 and the top part of its wall 46 is lifted above the level of the glass melt 8 (step D).

From the moment a set height above the surface 42 of the glass melt 8 is reached, the control device 22 continues to lift the dip pipe 10 with increased movement speed (see the curve section of the movement curve h(t) in FIG. 3 marked with the letter E) until the gas bubble separates from the glass melt 8, i.e. until the wall of the gas bubble tears away from the surface 42 of the glass melt 8 with at least one part of the wall of the gas bubble remaining on the dip pipe 10 as a film 48 that closes the former (step E). The dip pipe 10 is then lifted further until a predetermined height is reached at which the end of the dip pipe 10 enclosing the film 48 may be captured by an image capturing apparatus 52 during the cooling period of the film 48 (step F). From the moment in time $t_B$ at which this position is reached, the pressure in the dip pipe 10 is no longer controlled according to the given blow pressure curve but controlled by the control device 22 according to the data obtained by the image capturing device. The image capturing device 52 captures image data of the film 48 and transfers it to the control device 22. This control device then executes a comparison between the image data captured (actual data) and the target data saved. The control device 22 may also display the actual data and the target data through an output device 24, e.g. a monitor. The geometrical shape of the film 48 can be deducted by calculation with the operating program of the control device 22 serving to process the image data using an image or pattern detection algorithm and compared to the stored target data. On the basis of this comparison, the control device 22 controls the pressure setting device 26 until the film 48 solidifies into a firm membrane to adjust the geometry of the film to the target geometry corresponding to the target data saved. The target geometry may, for example, be a flat membrane.

Figure 4:
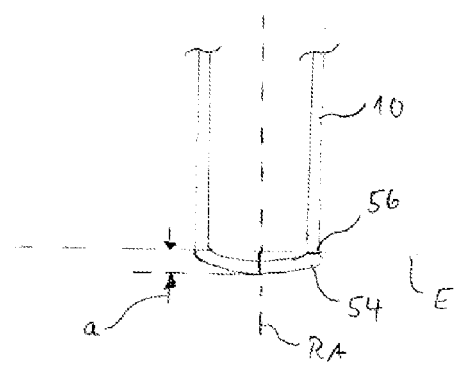
FIG. 4 is a schematic longitudinal section representation of a glass assembly with a flat membrane.

A glass assembly with a dip pipe 10 and a flat membrane 54 closing it at its end is schematically represented in FIG. 4. The dip pipe 10 shows a pipe axis RA which in the present example is a cylindrical symmetry axis. The outer surface of the flat membrane 54 does not have any point whose distance a from an imaginary level through the connection point 56 between the dip pipe 10 and the membrane 54 and vertically to the axis RA is more than 30% of the external diameter of the dip pipe 10.

Once the film 48 has solidified into a firm membrane, the actual geometry of the membrane may be captured again and compared to the target data. On the basis of this comparison, the control unit 22 may assign a classification which may especially be a measure of whether the assembly produced from the dip pipe 10 and the membrane must be regarded as a reject or may be used for the production of an electrochemical sensor. In the latter case, the assembly may be connected with other components to create an electrochemical sensor, especially a potentiometric pH sensor.

The invention claimed is:

1. A method for manufacturing a glass assembly, comprising:

lowering of a dip pipe vertically to a surface of a glass melt, the dip pipe having a distal end adjacent the surface of the glass melt;

determining when the surface of the glass melt is encountered by the distal end of the dip pipe by detecting an increase of a gas pressure inside the dip pipe;

after the distal end encounters the surface of the glass melt, continuing to lower the dip pipe until the distal end reaches a predetermined immersion depth into the glass melt;

holding the distal end at the immersion depth for a predetermined period;

applying a predetermined pressure inside the dip pipe, such that a gas bubble is created in the glass melt, the gas bubble having a wall attached to the distal end of the dip pipe;

after the predetermined period and while applying the predetermined pressure, lifting the dip pipe vertically with a predetermined first speed until the distal end is above the surface of the glass melt, such that an upper portion of the gas bubble wall is above the surface of the glass melt;

continuing to lift the dip pipe vertically above the surface of the glass melt until the upper portion of the gas bubble wall separates from the glass melt and remains at the distal end of the dip pipe as a film closing the distal end of the dip pipe; and controlling the predetermined pressure inside the dip pipe based on the geometry of the film as determined by an image capturing device.

2. The method according to claim 1, wherein:
the predetermined pressure follows a predetermined blow pressure curve of pressure as a function of time, and the blow pressure curve is saved in a control device.

3. The method according to claim 1, wherein:
the predetermined first speed used to lift the dip pipe during the application of the predetermined pressure follows a predetermined speed curve of speed as a function of time, the speed curve being saved in a control device or as a curve of movement providing a position of the dip pipe relative to the surface of the glass melt as a function of time.

4. The method according to claim 3, wherein:
the step of continuing to lift the dip pipe vertically above the surface of the glass melt includes lifting the dip pipe at a predetermined second speed, which is greater than the first speed.

5. The method according to claim 1, wherein:
the step of controlling the pressure inside the dip pipe based on the geometry of the film includes recording the actual geometry of the film using the image capturing device and comparing the actual geometry to saved target data that specify a target geometry of the film using a calculation program and an image processing device.

6. The method according to claim 5, wherein:
the saved target data describe a geometry of a flat membrane.

7. The method according to claim 1, wherein:
a glass pipe is used as the dip pipe.

8. The method according to claim 1, wherein:
the pressure on the inside of the dip pipe is controlled until the film has solidified to a firm membrane.

9. The method according to claim 8, wherein:
a glass assembly, including the dip pipe and the firm membrane, is manufactured as a wall enclosure component or assembly of an electrochemical sensor.

10. The method according to claim 1, wherein:
the film solidifies into a firm membrane, and wherein the method further comprises:

comparing the geometry of the firm membrane obtained with the image capturing device and the saved target data indicating a target membrane geometry; and
classifying the glass body based on the comparison.

11. The method according to claim 1, wherein:
the immersion depth, the period and/or the first speed are saved in a control unit configured to execute the method in a predetermined manner as selectable data, and wherein a setting device causes the lowering and lifting of the dip pipe being controlled accordingly.

12. The method according to claim 1, the method further comprising:
performing the method automatically using a pressure setting device, a setting device, which is embodied to receive the dip pipe and to lower and lift the dip pipe, and a control device configured to control the setting device and the pressure setting device for performing the method.

13. The method according to claim 1, wherein the pressure inside the dip pipe is controlled until the film closing the distal end of the dip pipe has solidified to a solid, substantially flat membrane.

* * * * *